(12) United States Patent
Ahn (10) Patent No.: US 8,257,392 B2
(45) Date of Patent: Sep. 4, 2012

(54) INTIMACY MEDICAL NEEDLE DESIGNED FOR NERVE STIMULATION THROUGH SOFT TISSUE AND MICROADHESIOLYSIS OF ADHERED SOFT TISSUE AND MEDICAL INSTRUMENT USING THE SAME

(76) Inventor: Kang Ahn, Seoul (KR)

( * ) Notice: Subject to any disclaimer, the term of this patent is extended or adjusted under 35 U.S.C. 154(b) by 344 days.

(21) Appl. No.: 11/629,038

(22) PCT Filed: Jun. 7, 2005

(86) PCT No.: PCT/KR2005/001692
§ 371 (c)(1),
(2), (4) Date: Sep. 12, 2008

(87) PCT Pub. No.: WO2005/120609
PCT Pub. Date: Dec. 22, 2005

(65) Prior Publication Data
US 2009/0216203 A1     Aug. 27, 2009

(30) Foreign Application Priority Data
Jun. 8, 2004   (KR) .................. 10-2004-0041689

(51) Int. Cl.
*A61B 17/34* (2006.01)
(52) U.S. Cl. ........................... 606/223; 606/185
(58) Field of Classification Search .......... 604/187, 604/264, 272–274; 606/167, 170, 185, 186, 606/188, 189, 222, 223
See application file for complete search history.

(56) References Cited

U.S. PATENT DOCUMENTS

| | | | |
|---|---|---|---|
| 2,409,979 A | 10/1946 | Huber | |
| 3,094,123 A * | 6/1963 | Kurtz | ............ 606/223 |
| 4,237,892 A * | 12/1980 | Ritter et al. | ............ 606/223 |
| 4,808,170 A | 2/1989 | Thornton et al. | |
| 5,575,780 A | 11/1996 | Saito | |
| 5,683,416 A * | 11/1997 | McGregor et al. | ............ 606/223 |
| 5,752,942 A | 5/1998 | Doyle et al. | |
| 7,070,583 B1 | 7/2006 | Higuchi et al. | |
| 2004/0030302 A1 | 2/2004 | Kamata et al. | |

FOREIGN PATENT DOCUMENTS

| | | |
|---|---|---|
| CN | 1140092 A | 1/1997 |
| CN | 1454103 A | 11/2003 |
| EP | 0 739 640 B1 | 7/2002 |
| EP | 1 297 856 A1 | 4/2003 |
| WO | WO 02/078772 A1 | 10/2002 |

* cited by examiner

*Primary Examiner* — Ryan Severson
(74) *Attorney, Agent, or Firm* — Edwards Wildman Palmer LLP

(57) ABSTRACT

A medical needle comprises a main body extending from a proximal end to a distal end, and a tip portion formed at the distal end of the body. The tip portion has a first inclined region, the cross-sectional area of which decreases toward the distal end and has a pair of surfaces inclined with an angle of 15° to 20°. The tip portion has a second inclined region extending from the first inclined region, the cross-sectional area of which decreases toward the distal end and has a pair of surfaces inclined with an angle of 30° to 45°. A tip is formed at the point of juncture of the pair of surfaces of the second inclined region. Tapered portions are formed on both sides of the first inclined region. Each tapered portion is inclined at an angle of 5° to 15°. Curved portions are formed at the points of juncture of the tip and the tapered portions.

21 Claims, 8 Drawing Sheets

(Prior Art)

Figure 10

(Prior Art)

INTIMACY MEDICAL NEEDLE DESIGNED FOR NERVE STIMULATION THROUGH SOFT TISSUE AND MICROADHESIOLYSIS OF ADHERED SOFT TISSUE AND MEDICAL INSTRUMENT USING THE SAME

TECHNICAL FIELD

The present invention generally relates to a medical needle, and more particularly to a medical needle for performing stimulation therapy and/or injection therapy on a certain region or point which induces pain and disabilities by inserting the needle into the pain region or point.

BACKGROUND ART

Chronic pain is a health problem that has been surging recently. Studies conducted thus far show that performing stimulation or injection therapy with a needle on a pain origin region or point is one of the effective way to treat or manage chronic pain.

An example of a therapeutic needle for musculoskeletal pain is disclosed in U.S. Pat. No. 2,409,979, which will be explained in view of FIGS. 9 and 10.

Figure 9:
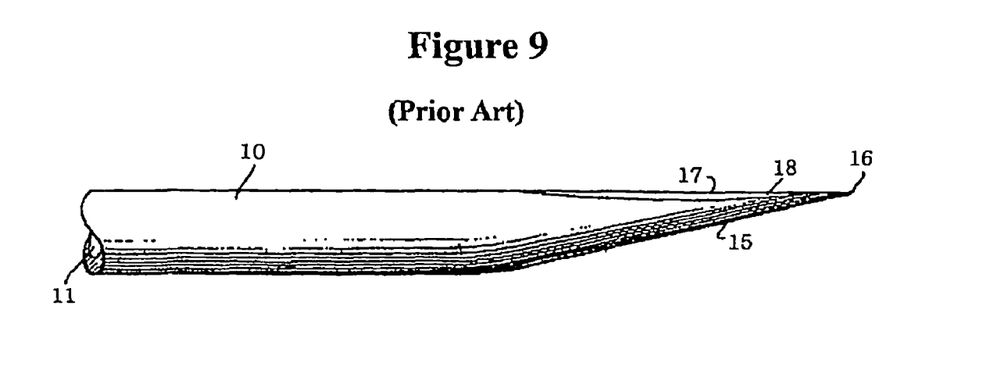
FIG. 9 is a side view of a medical needle of the prior art.
Figure 10:
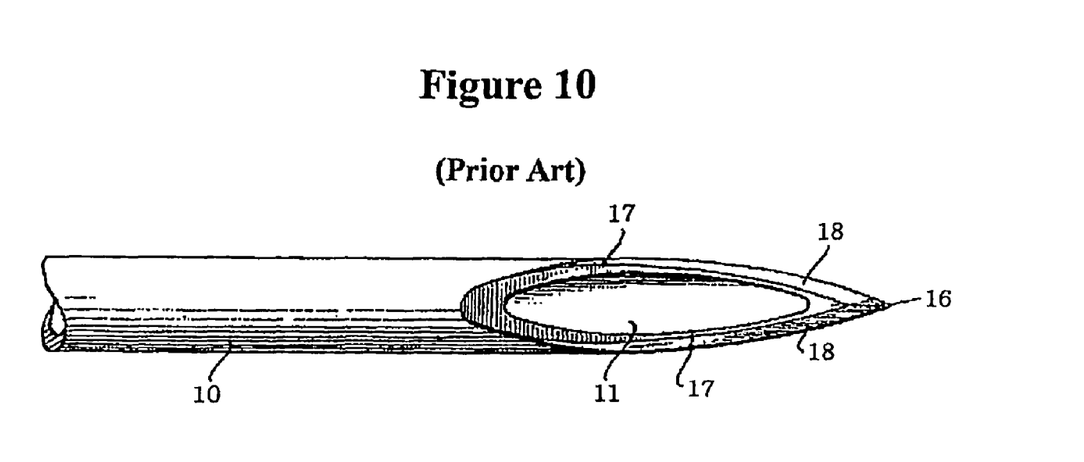
FIG. 10 is a plan view of the medical needle of the prior art.

As shown in FIGS. 9 and 10, a needle includes a body 10, which is circular in cross-section and which has a tubular bore 11, terminating in a discharge end or outlet defined by the edges of the wall of the body 10. The body 10 is bent to provide a curved surface 15 of diminishing area, extending in the direction of the outer parts of the end portion of the needle. This curved surface 15 is interrupted by the edges, which, at their points of merger with the curved surface 15, provide cutting edges 17. To provide the sharp cutting edges 17, beveled surfaces 18 extend at proper angles with respect to the curved surface 15. Accordingly, a slitting function is achieved as the needle is caused to pierce the tissue. A tissue-piercing point 16 is defined at the point of juncture of the surfaces 18 and 15.

However, while such a medical needle of prior art having sharp cutting edges and tissue-piercing point enters a patient's body to an object region or point, it can cause serious consequences such as severe bleeding due to penetration of blood vessel, serious neuropathy due to damage of nerves.

Particularly, when performing epidural anesthesia by using the medical needle of prior art, the needle should be inserted into an epidural space of a dura mater, which surrounds brain and spinal cord. During this procedure, there was a high risk of dural and arachnoidal laceration and corresponding CSF leakage with the sharp tissue-piercing point of the needle, which may lead to severe complication like a dural puncture headache. Also, when inserting the medical needle of prior art into the dura mater to extract cerebrospinal fluid, the sharp cutting edges and tissue-piercing point of the needle may damage the spinal cord and nerve roots surrounded by the dura mater, thereby causing serious problems such as physical paralysis and neuropathy.

Further, the medical needle of the prior art leaves many lacerations at the tissues since the sharp cutting edges split the tissues as it enters the patient's body.

DISCLOSURE OF THE INVENTION

Technical Problem

It is an object of the present invention to provide a medical needle designed to be inserted into a nerve, muscle or fascia, which is in need of stimulation therapy and/or injection therapy, while minimizing unwanted damage to the nerve or blood vessel.

It is another object of the present invention to provide a medical needle for performing epidural anesthesia or cerebrospinal fluid extraction, while minimizing side effects such as post dural puncture headache, neuropathy or physical paralysis.

It is yet another object of the present invention to provide a medical needle, which makes the nerves and vessels escape by themselves when contacting the needle.

It is yet another object of the present invention to provide a medical needle, which leaves little laceration at tissues as it is pushed to an object region or point inside the body without slitting the tissues.

It is yet another object of the present invention to provide a medical needle to impart a precise injection on the object region or point inside the body.

It is still yet another object of the present invention to provide a medical instrument using said medical needle.

Technical Solution

In order to achieve the above objects, the present invention provides a medical needle comprising a main body having a proximal end and a distal end, wherein the main body extends along a longitudinal axis from the proximal end to the distal end; and wherein a tip portion is formed at the distal end of the main body. The tip portion has a first inclined region, the cross-sectional area of which decreases progressively toward the distal end and has a pair of surfaces inclined with a first inclination angle. The tip portion also has a second inclined region extending from the end of the first inclined region toward the distal end, while the cross-sectional area decreases progressively toward the distal end and has a pair of surfaces inclined with a second inclination angle. Further, a tip is formed at the point of juncture of the pair of surfaces of the second inclined region and has a predetermined radius of curvature.

The main body is circular in cross-section. The diameter of the main body is 0.6 nm to 1.2 mm. Preferably, the first inclination angle is 15° to 20° and the second inclination angle is 30° to 45°.

The medical needle further comprises tapered portions, which are formed on parts of both sides of the first inclined region. Each tapered portion is inclined at a predetermined inclination angle with respect to the longitudinal axis, and curved portions are formed at the points of juncture of the tip and tapered portions, wherein the curved portions are rounded at a predetermined radius of curvature. Preferably, the inclination angle of each tapered portion is 5° to 15°.

A tubular bore for injection is formed through the main body and the tip portion along the longitudinal axis. The tip is located on the longitudinal axis, or is located apart from the longitudinal axis so that an opening of the tubular bore is located on one of the pair of surfaces of the first inclined region.

In order to achieve the above objects, a medical instrument of the present invention comprises a needle including a main body having a proximal end and a distal end. The main body extends along a longitudinal axis from the proximal end to the distal end, wherein a tip portion is formed at the distal end of the main body. The tip portion has a first inclined region, the cross-sectional area of which decreases progressively toward the distal end and has a pair of surfaces inclined with a first inclination angle. A second inclined region extends from the end of the first inclined region toward the distal end, while the cross-sectional area decreases progressively toward the distal end and has a pair of surfaces inclined with a second inclination angle. A tip is formed at the point of juncture of the pair of surfaces of the second inclined region and has a predetermined radius of curvature. The medical instrument of the present invention also comprises a moving unit including a griping part, an extending part extending from the griping part, and a supporting part provided at the end of the extending part and to which the proximal end of the main body of the needle is fixed. It further comprises a guiding unit including a hollow receiving part, into which the moving unit is inserted to be moved linearly, and a bending-prevention part extending from the end of the receiving part for guiding the movement of the needle.

BEST MODE

Preferred embodiments of the present invention will now be described in detail with reference to the accompanying drawings.

Figure 1:
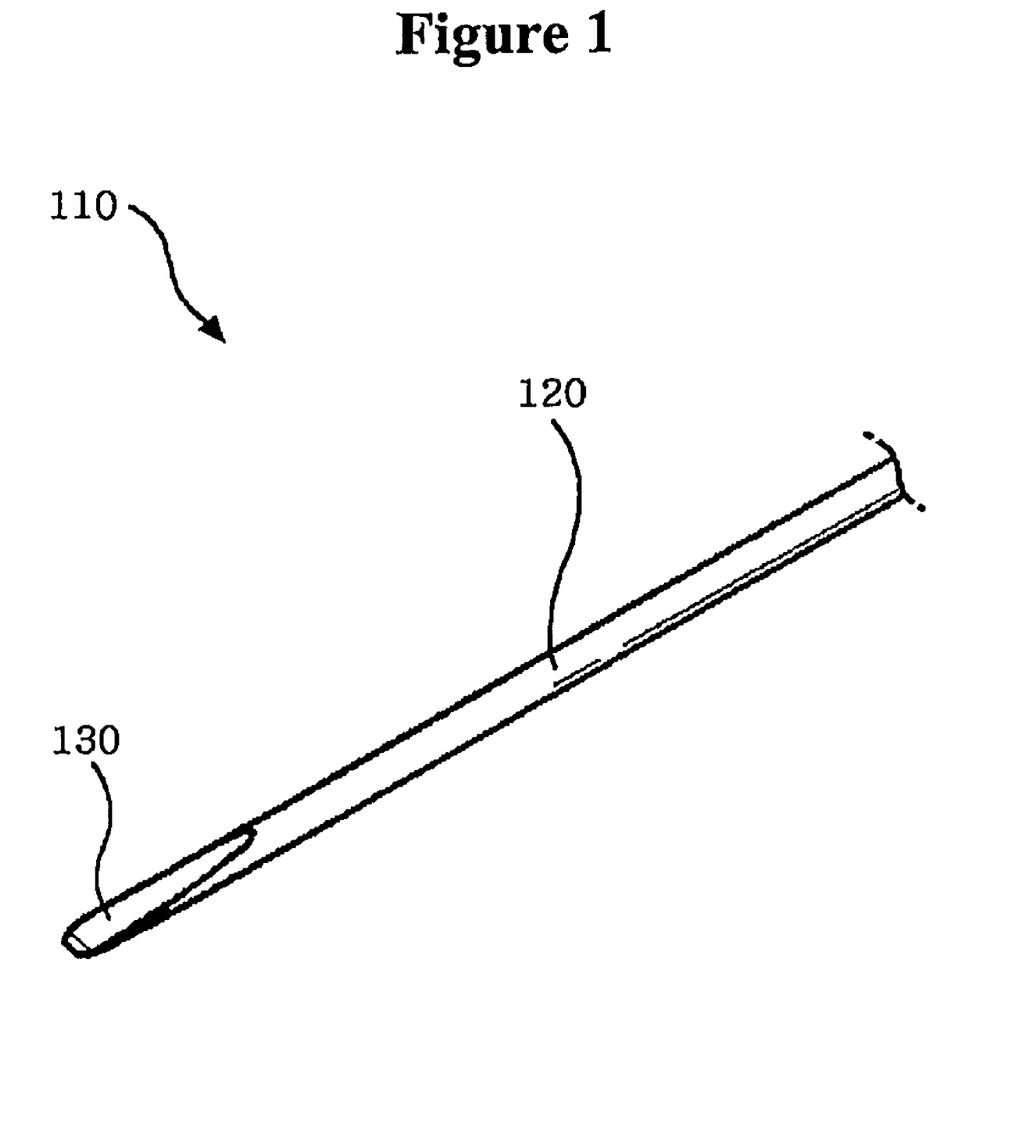
FIG. 1 is a perspective view of a medical needle constructed in accordance with a first embodiment of the present invention.

FIG. 1 is a perspective view of a medical needle constructed according to a first embodiment of the present invention.

As shown in the drawing, the medical needle 110 of the first embodiment of the present invention has a main body 120, which is circular in cross-section and extends to a predetermined length, wherein a tip portion 130 is formed at the front end portion of the body 120.

Hereinafter, the portion closest to the user (i.e., the surgeon) in each part of the medical needle 110 will be defined as the proximal end portion, while the portion farthest from the user in each part will be defined as the distal end portion.

Figure 2:
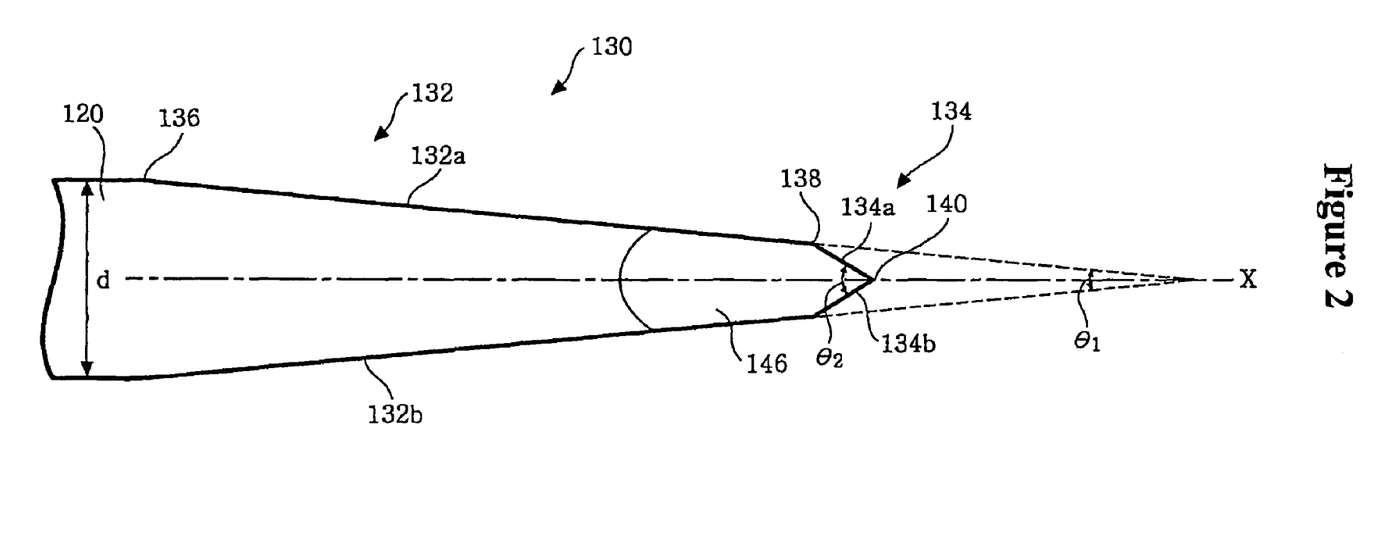
FIG. 2 is a side view of the medical needle shown in FIG. 1.
Figure 3:
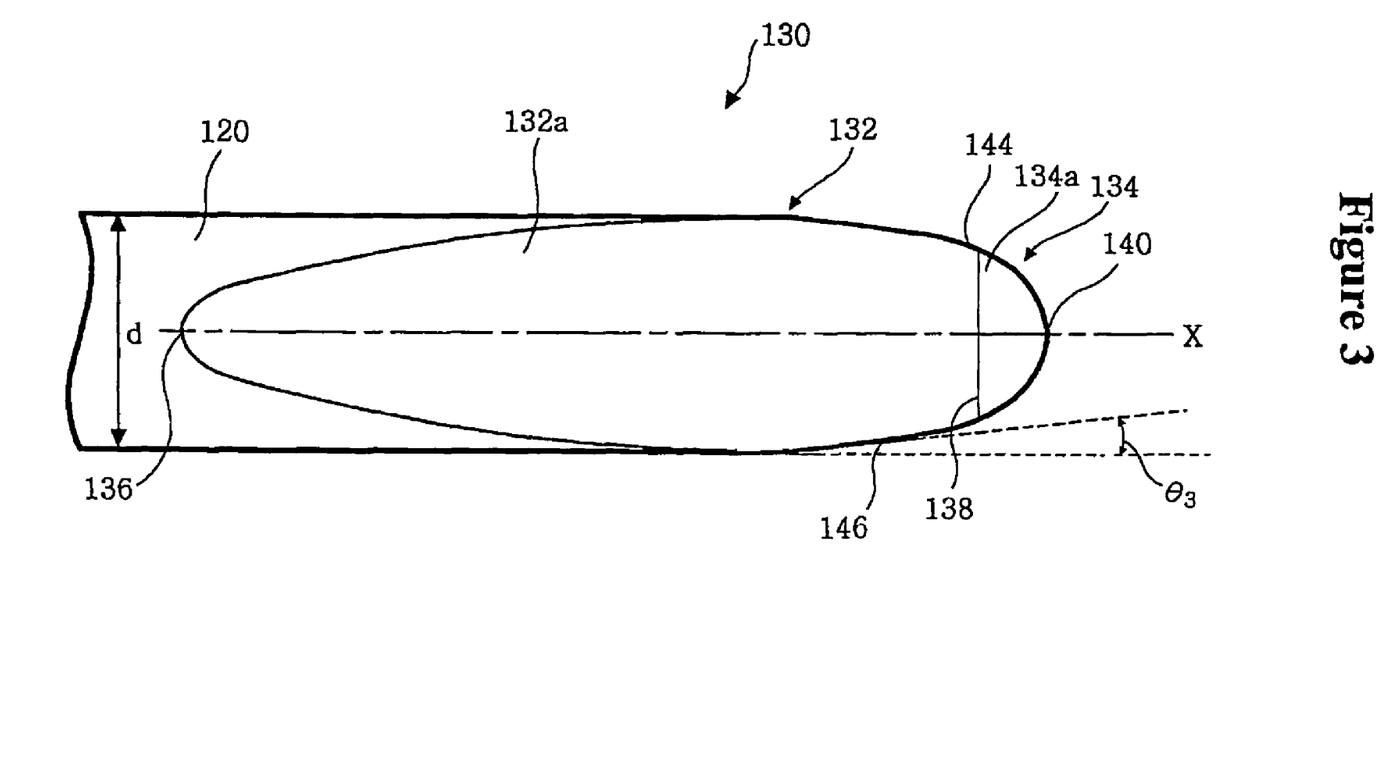
FIG. 3 is a plan view of the medical needle shown in FIG. 1.

FIG. 2 and FIG. 3 are a side view and a plan view of the medical needle shown in FIG. 1, respectively.

As shown in the drawings, the tip portion 130 includes a first inclined region 132 and an integral second inclined region 134. The cross-sectional area of the first inclined region 132 decreases progressively from its proximal ends 136 on a circumference of the main body 120 to its distal ends 138. The first inclined region 132 includes an upper inclined surface 132a and a lower inclined surface 132b, which are bilaterally symmetric on a longitudinal axis X which passes through the center of the circular main body 120 (refer to FIG. 2). Preferably, the diameter d of the main body 120 is approximately 0.6 mm~1.2 mm, and the inclination angle $\theta_1$ made by the upper and lower inclined surfaces 132a and 132b of the first inclined region 132 is approximately 15°~20°.

Similar to the first inclined region 132, the cross-sectional area of the second inclined region 134 decreases progressively from its proximal ends 138 to its distal end 140 and includes an upper inclined surface 134a and a lower inclined surface 134b, which are bilaterally symmetric on the longitudinal axis X of the main body 120 (refer to FIG. 2). The proximal ends 138 of the second inclined region 134 are the same points as the distal ends of the first inclined region 132. The distal end 140 of the second inclined region 134 is the tip, which is configured to permit piercing of the patient's skin. Preferably, an inclination angle $\theta_2$ made by the upper and lower inclined surfaces 134a and 134b of the second inclined region 134 is approximately 30°~45°.

As shown in FIG. 3, there are provided tapered portions 146 on parts of both sides of the first inclined region 132. Each tapered portion 146 is inclined at a predetermined angle $\theta_3$ with respect to the longitudinal axis X of the main body 120. Also, the tip 140 is positioned on the longitudinal axis X (refer to FIG. 2) of the body 120 and has a prescribed radius of curvature. Curved portions 144 are formed at the points of juncture of the tip 140 and the tapered portions 146, which are rounded at a prescribed radius of curvature. It is desirable for the inclination angle $\theta_3$ of the tapered portion 146 to be approximately 5°~15°.

The side surfaces of the first inclined region 132 of the tip portion 130 are round, but the tip 140 is shaped flat and sharp due to the second inclined region 134. However, the tip 140 becomes rounder and blunter as it goes from its center to the curved portions 144. As explained above, since the center of the tip 140 is sharp but flat, it is used only to pierce through the patient's skin, and not to perforate the nerve or blood vessel. This minimizes the damage on the nerve or blood vessel. Moreover, since the tip 140 becomes rounder and blunter from its center to the curved portions 144 and the tapered portions 146, the needle does not slit the tissue but rather pushes therethrough as it progresses to the object region or point, thus causing little injury to the tissue.

The needle, which is constructed in accordance with the first embodiment of the present invention, is used for treating the following symptoms. The operational effects will also be explained below.

First, the medical needle of the present invention is used for treating a nerve capture. Particularly, the needle can be inserted in the soft tissue of fibrosis around the spine to stimulate the soft tissue and also to release the tangled tissue by rotating the needle. Upon doing so, the medical needle of the present invention does not slit the tissue by its characteristics in shape, but rather pushes through the tissue (as explained above). This operational effect is very important for treating regions around the spine.

Second, the medical needle of the present invention is used for treating microadhesiolysis of muscles. Muscles with contraction knots are very hard and strained. The conventional medical needle with an acute tip (refer to FIGS. 9 and 10) is unsafe when it is inserted in order to release contraction knots. More particularly, approaching the spinal tonic muscle, such as multifidus, is very precarious since the acute conventional needle can penetrate into the spine or injure the nerves of the spine. However, the medical needle of the present invention, as explained above, does not easily slit or pierce the nerve or blood vessel and makes the nerve or blood vessel escape by itself when contacting the needle due to the characteristics of its shape. Thus, it is possible to approach the spinal tonic muscle and effectively release the contraction knots.

Lastly, the medical needle of the present invention is used for treating tangles of fascia, ligament or tendon. For example, the collagen fiber that composes the tendon is folded, wrinkled or tangled on the insertion point where the tendon is attached to the bone. In such a region, the collagen fiber adheres to the surrounding soft tissue. In order to induce the reproduction of the collagen fiber, the adhesion to the surrounding soft tissue should be broken. In such a situation, the medical needle of the present invention can widen the space between the tangled soft tissues or tear apart the tangled tissues by winding and rotating the same without slitting the soft tissue, thereby minimizing the injury of the tissue. Moreover, the flat and round shapes of the tip 140 and the curved portions 144 enable an operator to better feel the resistance of the soft tissue.

Figure 4:
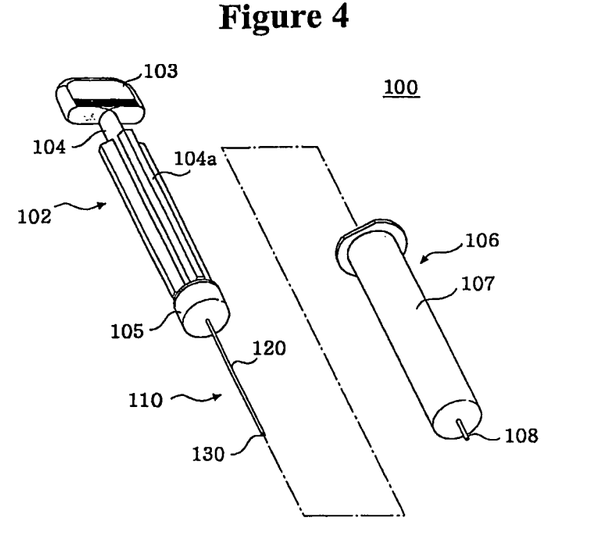
FIG. 4 is a perspective view of a medical instrument using the medical needle shown in FIG. 1.

FIG. 4 is a perspective view of a medical instrument using the medical needle 110.

As shown in the drawing, the medical instrument 100 comprises the needle 110, a moving unit 102 for supporting the needle 110 for easy movement of the needle 110, and a guiding unit 106 for guiding the movement of the moving unit 102.

The moving unit 102 includes a griping part 103, which is flat and rectangular in cross-section so that the user can hold it with the user's hands, an extending part 104, which extends from a side surface of the griping part 103, and a supporting part 105, which is provided at the end of the extending part 104 and to which the end of the body 120 of the needle opposite to the tip portion 130 is fixed. The guiding unit 106 includes a hollow cylinder-shaped receiving part 107, one end of which is opened for receiving the extending part 104 and the supporting part 105 of the moving unit 102, and a bending-prevention part 108, which extends longitudinally from the other end of the receiving part 107 and surrounds a part of the needle 110.

Preferably, the extending part 104 of the moving unit 102 is formed in a piston shape, which is inserted into the receiving part 107 of the guiding unit 106. The extending part 104 has ribs 104a, which protrude radially and extend longitudinally on the peripheral surface of the extending part 104. The height of the rib 104a is designed so that the top ends of the ribs 104a simultaneously contact the inner surface of the receiving part 107. Forming such ribs 104a on the peripheral surface of the extending part 104 is for accurately moving the moving unit 102 along the inner surface of the receiving part 107 and reducing the friction with the inner surface of the receiving part 107 for smoother linear movement of the moving unit 102. Although it is illustrated in FIG. 4 that three or four ribs 104a are provided symmetrically on the extending part 104, the number, shape or arrangement of the ribs may be varied according to the size of the entire medical instrument 100, etc.

The supporting part 105 is circular in cross-section and is desirable to be slightly smaller than the inner diameter of the receiving part 107 of the guiding unit 106. This is so that the air can freely flow through a gap between the supporting part 105 and the receiving part 107 when the moving unit 102 reciprocates linearly in the receiving part 107. The supporting part 105 may be formed integrally at the end of the extending part 104, or detachably coupled to the end of the extending part 104. Since the needle 110 can vary in size (e.g., the diameter) according to the region to be treated or the purpose of the treatment, it is more cost-effective to manufacture supporting parts 105 integrated with various needles 110 than to manufacture the whole moving units 102 integrated with supporting parts 105 and various needles 110. In other words, each independent supporting part 105 having a needle 110 can be replaced depending on each treatment situation in such a manner that the supporting part 105 is coupled detachably to the end of the common-used extending part 104 by means of screw-coupling, press-fitting or the like. The medical instrument 110 of the present invention could be produced with various materials having certain solidity and proven to be harmless to the human body. Preferably, the needle 110 is made of stainless steel, and the moving unit 102 and the guiding unit 106 are made of synthetic resins.

The user inserts the needle 110, the supporting part 105 and the extending part 104 of the moving unit 102 into the receiving part 107 of the guiding unit 106, and locates the bending-prevention part 108 of the receiving part 107 on the surface of the patient's body approximate to the region to be treated. If the user fixes the location of the receiving part 107 with one hand, and holds the griping part 103 of the moving unit 102 and pushes the moving unit 102 toward the patient's body with the other hand, the moving unit 102 moves linearly while the ribs 104a contact the inner surface of the receiving part 107. At the same time, the needle 110 passes through the bending-prevention part 108 and progresses toward the tissue inside the patient's body for treatment, as explained above. The needle 110 can go straight in the patient's body without bending since the bending-prevention part 108 has a predetermined length, which can enhance the therapeutic effect and convenience of usage.

Figure 5:
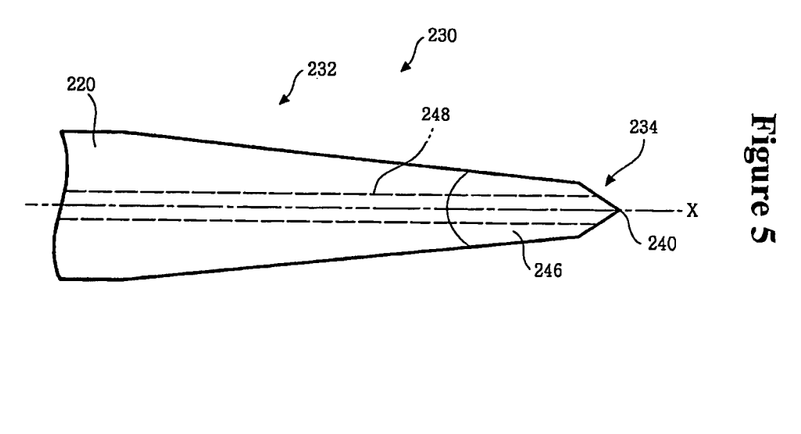
FIG. 5 is a side view of a medical needle constructed according to a second embodiment of the present invention.
Figure 6:
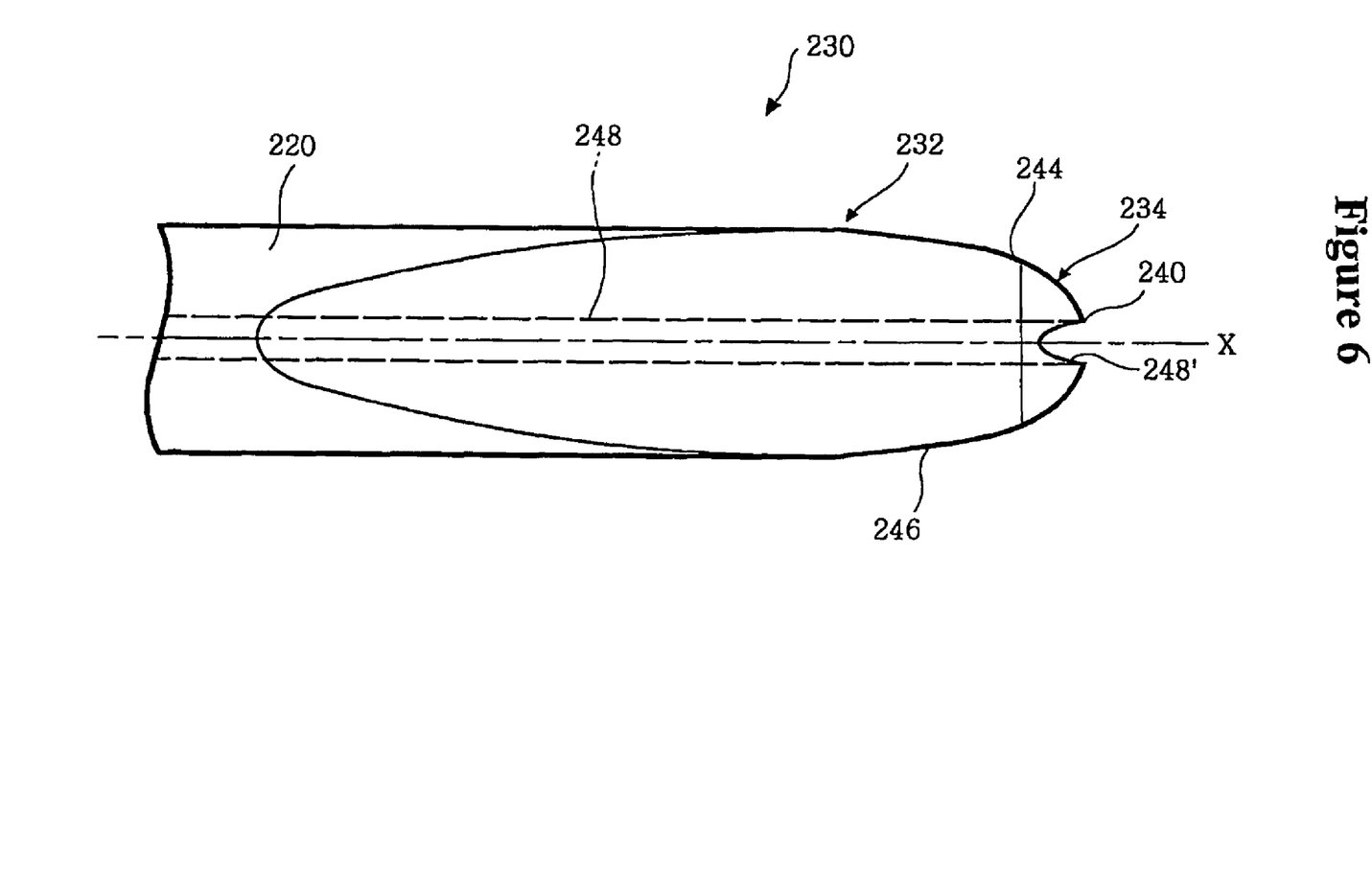
FIG. 6 is a plan view of the medical needle constructed according to the second embodiment of the present invention.

FIG. 5 and FIG. 6 are a side view and a plan view of a medical needle according to a second embodiment of the present invention, respectively.

As shown in the drawings, the medical needle according to the second embodiment of the present invention comprises a main body 220 and a tip portion 230 having first and second inclined regions 232 and 234, a tip 240, tapered portions 246 and curved portions 244, similar to the medical needle 110 of the first embodiment. The medical needle according to the second embodiment further comprises a tubular bore 248 for injection. The tubular bore 248 is formed through the main body 220 and the tip portion 230 along the longitudinal axis X.

In addition to the therapeutic effects described above in association with the first embodiment, the medical needle of the second embodiment provides certain effects such as administering anesthesia or injection in a region to be treated in a human body or sampling of cerebrospinal fluid. Particularly, when the medical needle is inserted into an epidural space of a dura mater to perform epidural anesthesia, the flat and rounded tip 240 and curved portions 244 have little possibility of penetrating the dura mater, thus preventing severe headache which may be caused by penetrating the dura mater. Moreover, when inserting the needle toward the dura matter to extract the cerebrospinal fluid, the spinal cord and nerve roots are not injured by the shape of the needle, thus preventing severe side effects such as physical paralysis or neuropathy of the patient.

Since an opening 248' of the tubular bore 248 for injection is positioned at the tip 240, the injection can emit straight from the tip 240, thereby enabling precise injection into the object region or point and minimizing the loss of injection into surrounding tissues.

The explanation and drawings of the apparatus or instrument, to which the needle is connected for performing injections or sampling cerebrospinal fluid through the bore 248, are omitted herein since it is well known in the art.

Figure 7:
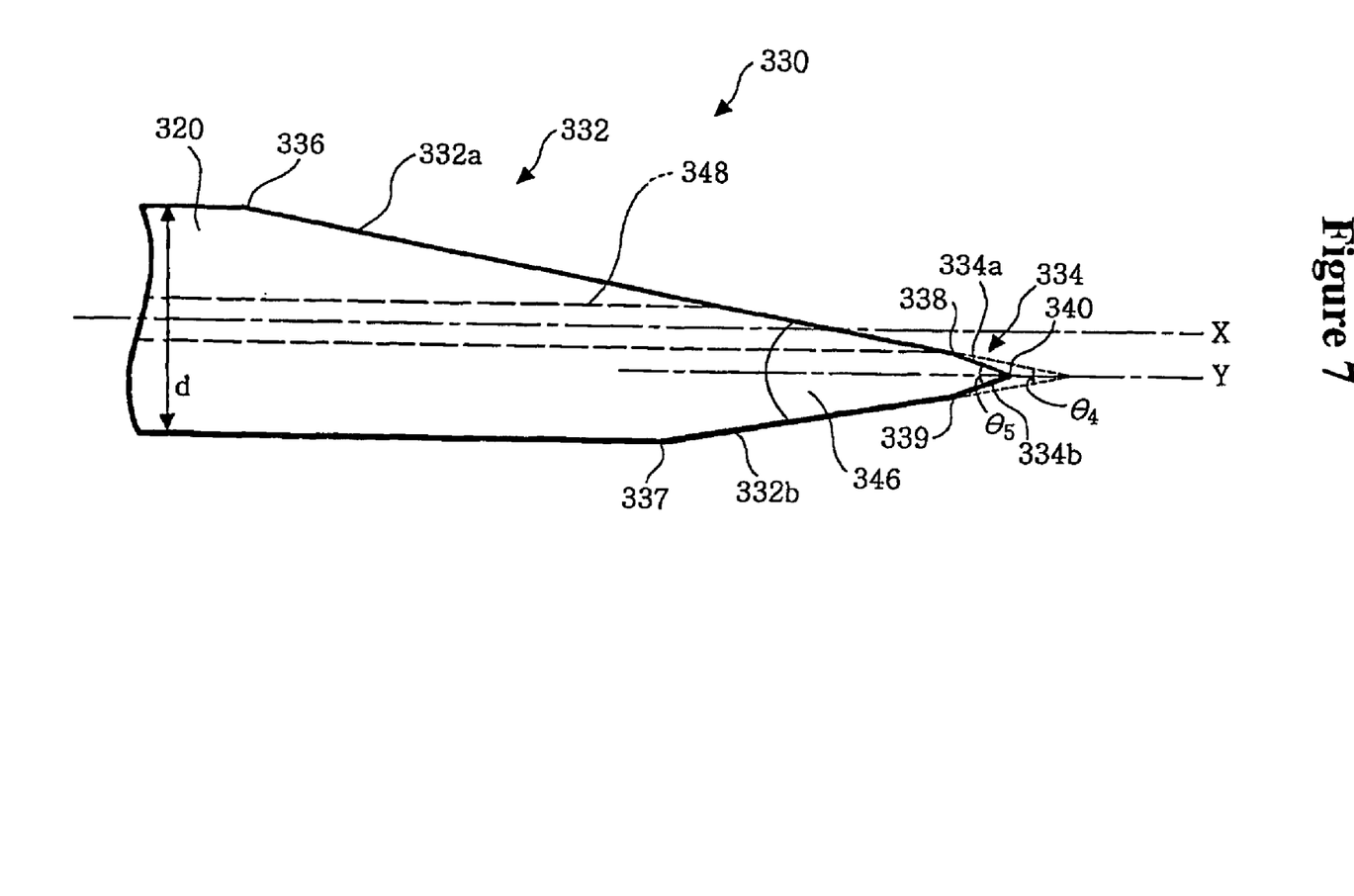
FIG. 7 is a side view of a medical needle constructed in accordance with a third embodiment of the present invention.
Figure 8:
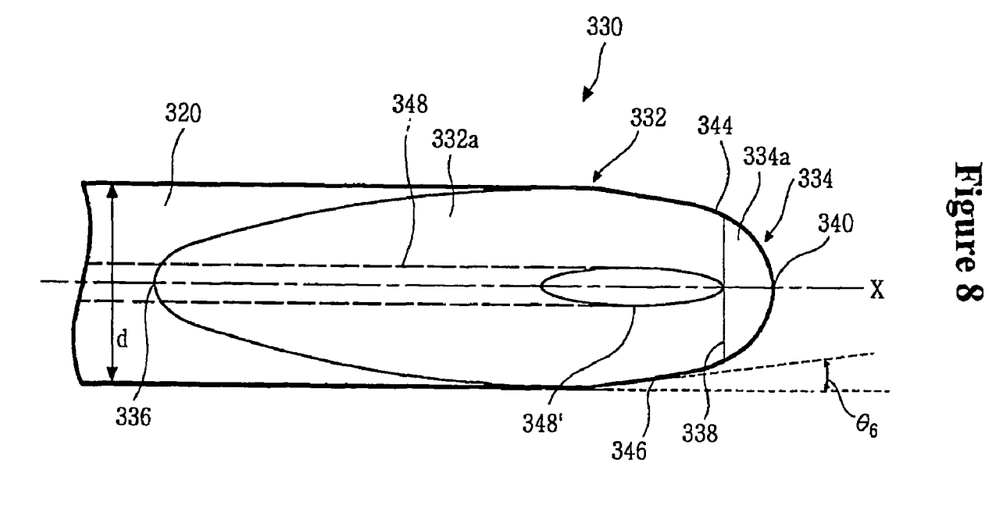
FIG. 8 is a plan view of the medical needle constructed according to the third embodiment of the present invention.

FIG. 7 and FIG. 8 are a side view and a plan view of a medical needle constructed according to a third embodiment of the present invention, respectively.

As shown in the drawings, the medical needle according to the third embodiment has a main body 320, which is circular in cross-section and extends to a predetermined length. It also has a tip portion 330, which is formed at the front end portion of the main body 320.

The tip portion 330 includes a first inclined region 332 and an integral second inclined region 334. The cross-sectional area of the first inclined region 332 decreases progressively from its proximal ends 336 and 337 on the circumference of the main body 320 to its distal ends 338, 339. The first inclined region 332 includes an upper inclined surface 332a and a lower inclined surface 332b. The upper inclined surface 332a is inclined downward at a prescribed angle from its proximal end 336 located above the longitudinal axis X to its distal end 338 located below the longitudinal axis X, whereas the lower inclined surface 332b is inclined upward from its proximal end 337 to its distal end 339. Preferably, the diameter d of the main body 320 is approximately 0.6 mm~1.2 mm, and the inclination angle $\theta_4$ made by the upper inclined surface 332a and the lower inclined surface 332b of the first inclined region is approximately 15° to 20°.

Similar to the first inclined region 332, the cross-sectional area of the second inclined region 334 decreases progressively from its proximal ends 338 and 339 to its distal end 340. The second inclined region 334 includes an upper inclined surface 334a and a lower inclined surface 334b, which are bilaterally symmetric on a longitudinal axis Y, which passes through the distal end 340 of the second inclined region 334 (refer to FIG. 7). The proximal ends 338, 339 of the second inclined region 334 are located at the same points as the distal ends of the first inclined region 332. Further, the distal end 340 is a tip, which is configured to permit piercing of the patient's skin. Preferably, the inclination angle $\theta_5$ made by the upper and lower inclined surfaces 334a and 334b of the second inclined region 334 is approximately 30° to 45°.

As shown in FIG. 8, there are provided tapered portions 346 on parts of both sides of the first inclined region 332. Each tapered portion 346 is inclined at a predetermined angle $\theta_6$ with respect to the longitudinal axis X. The tip 340 is positioned below the axis X (refer to FIG. 7), and has a prescribed radius of curvature. Curved portions 344 are formed at the points of juncture of the tip 340 and the tapered portions 346, which are rounded at a prescribed radius of curvature. It is desirable for the inclination angle $\theta_6$ of the tapered portion 346 to be approximately 5°~15°.

A tubular bore 348 for injection is formed through the main body 320 and the tip portion 330 along the longitudinal axis X. An opening 348' of the bore 348 is exposed outside on the upper inclined surface 332a of the first inclined region 332, as shown in FIG. 8. The explanation and drawings of the apparatus or instrument, to which the needle is connected for performing injections or sampling cerebrospinal fluid through the bore 348, are omitted herein since it is well known in the art.

The side surfaces of the first inclined region 332 of the tip portion 330 are round, but the tip 340 is shaped flat and sharp due to the second inclined region 334. However, the tip 340 becomes rounder and blunter as it goes from its center to the curved portions 344. As explained above, since the center of the tip 340 is sharp but flat, it is used only to pierce through the patient's skin, and hardly to perforate the nerve or blood vessel, thus minimizing the damage on the nerve or blood vessel. Moreover, since the tip 340 becomes rounder and blunter from its center to the curved portions 344 and the tapered portions 346, the needle does not slit the tissue but pushes therethrough as it progresses to the object region or point, thus causing little injury to the tissue.

The medical needle of the third embodiment is advantageous in that no fiber tissues such as fascia can get caught in the opening 348' of the bore 348 since the opening 348' is located on the upper inclined surface 332a of the first inclined region 332 (as opposed to the needle of the above-described second embodiment, in which the opening 248' of the bore 248 is located at the tip 240). Therefore, the needle of the second embodiment is more appropriate for treating the articular region where important nerve or blood vessels are not much distributed, whereas the needle of the third embodiment is more appropriate for treating the nerve roots of the spine, etc.

INDUSTRIAL APPLICABILITY

As explained above in detail, the center of the tip is sharp but flat. As such, when the medical needle of the present invention is inserted into a nerve, muscle or fascia, which is in need of stimulation therapy and/or injection therapy, it is used only to pierce through the patient's skin, and hardly to perforate the nerve or blood vessel, thus minimizing the damage on the nerve or blood vessel.

Also, since the tip becomes rounder and blunter from its center to the curved portions and the tapered portions, the needle does not slit the tissue, but rather pushes therethrough as it progresses to the object region or point, thus causing little injury to the tissue.

In addition, when the medical needle is inserted into an epidural space of a dura mater to perform epidural anesthesia, the flat and rounded tip and curved portions have little possibility of penetrating the dura mater, thus preventing severe headache which may be caused by penetrating the dura mater. Moreover, when inserting the needle toward the dura matter to extract the cerebrospinal fluid, the spinal cord and nerve roots are not injured by the characteristics in the shape of the needle, thus preventing severe side effects such as physical paralysis or neuropathy of the patient.

Furthermore, since the injection can emit straight from the tip, it enables precise injection into the object region or point and minimizes the loss of injection into surrounding tissues.

The invention claimed is:

1. A medical needle, comprising: a main body having a proximal end and a distal end, the main body extending along a longitudinal axis from the proximal end to the distal end; and a tip portion formed at the distal end of the main body,
wherein the tip portion comprises:
a first inclined region having a proximal end connected to the distal end of the main body and a distal end, having cross-sectional area decreasing progressively from the proximal end thereof toward the distal end thereof, and having upper and lower surfaces that are flat and inclined a first predetermined angle with respect to the longitudinal axis;
a second inclined region having a proximal end connected to the distal end of the first inclined region and a distal end, having cross-sectional area decreasing progressively from the proximal end thereof toward the distal end thereof, having upper and lower surfaces that are flat and inclined at a second predetermined angle with respect to the longitudinal axis, and having side surfaces each of which has a curved portion rounded at a predetermined radius of curvature; and
a tip formed at the distal end of the second inclined region and having a distal end,
wherein upper and lower surfaces of the tip are flat and close to each other such that the distal end of the tip is flat and sharp and side surfaces of the tip become rounder and blunter as they go toward the curved portions of the inclined region.

2. The medical needle of claim 1, wherein the main body is circular in cross-section and the diameter of the main body is 0.6 mm to 1.2 mm.

3. The medical needle of claim 2, wherein the first inclined region has side surfaces each of which has a tapered portion inclined at a predetermined inclination angle with respect to the longitudinal axis, such that the curved portions are formed at the points of juncture of the tip and the tapered portions.

4. The medical needle of claim 1, wherein the first inclination angle is 15 degree to 20 degree and the second inclination angle is 30 degree to 45 degree.

5. The medical needle of claim 4, wherein the first inclined region has side surfaces each of which has a tapered portion inclined at a predetermined inclination angle with respect to the longitudinal axis, such that the curved portions are formed at the points of juncture of the tip and the tapered portions.

6. The medical needle of claim 1, wherein the first inclined region has side surfaces each of which has a tapered portion inclined at a predetermined inclination angle with respect to the longitudinal axis, such that the curved portions are formed at the points of juncture of the tip and the tapered portions.

7. The medical needle of claim 6, wherein the inclination angle of each tapered portion is 5 degree to 15 degree.

8. The medical needle of claim 6, wherein a tubular bore for injection is formed through the main body and the tip portion along the longitudinal axis.

9. The medical needle of claim 8, wherein the tip is located on the longitudinal axis.

10. The medical needle of claim 8, wherein an opening of the tubular bore is located on one of the pairs of surfaces of the first inclined region.

11. A medical instrument, comprising:
a needle including a main body having a proximal end and a distal end, the main body extending along a longitudinal axis from the proximal end to the distal end and a tip portion being formed at the distal end of the main body;
a moving unit including a griping part, an extending part extending from the griping part, and a supporting part provided at the end of the extending part and to which the proximal end of the main body of the needle is fixed; and
a guiding unit including a hollow receiving part, into which the moving unit is able to be inserted to be moved linearly, and a bending-prevention part extending from the end of the receiving part for guiding the movement of the needle
wherein the tip portion comprises:
a first inclined region having a proximal end connected to the distal end of the main body and a distal end, having cross-sectional area decreasing progressively from the proximal end thereof toward the distal end thereof, and having upper and lower surfaces that are flat and inclined at a first predetermined angle with respect to the longitudinal axis;
a second inclined region having a proximal end connected to the distal end of the first inclined region and a distal end, having cross-sectional area decreasing progressively from the proximal end thereof toward the distal end thereof, having upper and lower surfaces that are flat and inclined at a second predetermined angle with respect to the longitudinal axis, and having side surfaces each of which has a curved portion rounded at a predetermined radius of curvature; and
a tip formed at the distal end of the second inclined region and having a distal end,
wherein upper and lower surfaces of the tip are flat and close to each other such that the distal end of the tip is flat and sharp and side surfaces of the tip become rounder and blunter as they go toward the curved portions of the inclined region.

12. The medical instrument in claim 11, wherein the main body is circular in cross-section and the diameter of the main body is 0.6 mm to 1.2 mm.

13. The medical instrument of claim 12, wherein the first inclined region has side surfaces each of which has a tapered portion inclined at a predetermined inclination angle with respect to the longitudinal axis, such that the curved portions are formed at the points of juncture of the tip and the tapered portions.

14. The medical instrument of claim 11, wherein the first inclination angle is 15 degree to 20 degree and the second inclination angle is 30 degree to 45 degree.

15. The medical instrument of claim 14, wherein the first inclined region has side surfaces each of which has a tapered portion inclined at a predetermined inclination angle with respect to the longitudinal axis, such that the curved portions are formed at the points of juncture of the tip and the tapered portions.

16. The medical instrument of claim 11, wherein the first inclined region has side surfaces each of which has a tapered portion inclined at a predetermined inclination angle with respect to the longitudinal axis, such that the curved portions are formed at the points of juncture of the tip and the tapered portions.

17. The medical instrument of claim 16, wherein the inclination angle of each tapered portion is 5 degree to 15 degree.

18. The medical instrument of claim 11, wherein ribs protrude radially and extend longitudinally on the peripheral surface of the extending part and simultaneously contact the inner surface of the receiving part.

19. The medical instrument of claim 18, wherein the supporting part is detachably coupled to the end of the extending part.

20. The medical instrument of claim 11, wherein the supporting part is detachably coupled to the end of the extending part.

21. A medical needle comprising a main body having a proximal end and a distal end and extending along a longitudinal axis from the proximal end to the distal end and a tip portion formed at the distal end of the main body,
where the tip portion comprises:
an inclined region having an upper surface that is flat and inclined at a first predetermined angle, a lower surface that is flat and inclined at a second predetermined angle that is the same as or different from the first predetermined angle, and side surfaces each of which has a curved portion rounded at a predetermined radius of curvature; and
a tip formed at an end of the inclined region,
wherein upper and lower surfaces of the tip are flat and close to each other such that the distal end of the tip is flat and sharp and side surfaces of the tip become rounder and blunter as they go toward the curved portions of the inclined region.

* * * * *